United States Patent
Labgold et al.

(10) Patent No.: US 11,385,226 B2
(45) Date of Patent: *Jul. 12, 2022

(54) SELF-ACTUATING SIGNAL PRODUCING DETECTION DEVICES AND METHODS

(75) Inventors: Marc Robert Labgold, Reston, VA (US); George G. Jokhadze, Menlo Park, CA (US)

(73) Assignee: RED IVORY LLC, Honolulu, HI (US)

( * ) Notice: Subject to any disclaimer, the term of this patent is extended or adjusted under 35 U.S.C. 154(b) by 1284 days.

This patent is subject to a terminal disclaimer.

(21) Appl. No.: 12/212,007

(22) Filed: Sep. 17, 2008

(65) Prior Publication Data

US 2009/0107852 A1     Apr. 30, 2009

Related U.S. Application Data

(60) Provisional application No. 61/123,280, filed on Apr. 7, 2008, provisional application No. 60/960,112, filed on Sep. 17, 2007.

(51) Int. Cl.
*G01N 33/543* (2006.01)
*C12Q 1/6825* (2018.01)

(52) U.S. Cl.
CPC ....... *G01N 33/5438* (2013.01); *C12Q 1/6825* (2013.01)

(58) Field of Classification Search
CPC . G01N 33/5438; G01N 27/3275–3278; C12Q 1/6825
USPC ................................ 435/5, 6; 205/777.5, 775
See application file for complete search history.

(56) References Cited

U.S. PATENT DOCUMENTS

| | | | |
|---|---|---|---|
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,516,644 A * | 5/1996 | Yamauchi et al. | ............. 435/7.9 |
| 5,593,852 A | 1/1997 | Heller et al. | |
| 5,665,222 A | 9/1997 | Heller et al. | |

(Continued)

OTHER PUBLICATIONS

Boiteux, J. L. and Thomas, D., Oxygen Electrode-Based Enzyme Immunoassay for the Amperometric Determination of Hepatitis B Surface Antigen, Analytica Chimica Acta, 163 (1984) 309-313.*

(Continued)

*Primary Examiner* — Maris R Kessel
(74) *Attorney, Agent, or Firm* — The Kelber Law Group; Steven B. Kelber

(57) ABSTRACT

An assay system is provided of great sensitivity and portability where the presence of a specific target in a sample, as well as its concentration (qualification and quantification) is detected by reason of a potential or voltage in a closed circuit, built up a redox reaction. The reaction is produced by binding a capture moiety to an enzymatic redox reaction partner, allowing the capture moiety to bind to any target in the sample. In a homogenous assay, the method further comprises washing any such bound target. The bound target may be immobilized through use of a second capture moiety. Substrate for the enzyme is then added. The action on the substrate by the enzyme generates electrons, creating a potential across an anode and cathode which may be separated by a membrane.

14 Claims, 9 Drawing Sheets

Specification includes a Sequence Listing.

(56) References Cited

U.S. PATENT DOCUMENTS

| | | | | |
|---|---|---|---|---|
| 2006/0160100 | A1* | 7/2006 | Gao | B82Y 30/00 |
| | | | | 435/6.11 |
| 2006/0266645 | A1* | 11/2006 | Chen et al. | 204/403.01 |
| 2007/0231794 | A1* | 10/2007 | Dill | C12Q 1/6825 |
| | | | | 435/6.11 |
| 2008/0038749 | A1* | 2/2008 | Fleischer | G01N 33/5438 |
| | | | | 435/7.1 |
| 2009/0061451 | A1* | 3/2009 | Achim | G01N 33/5438 |
| | | | | 435/6.11 |

OTHER PUBLICATIONS

G.A. Robinson, H.A.O. Hill, R.D. Phillo, J.M. Gear, S.J. Rattle and G.C. Forrest, Biolelectrochemical Enzyme Immunoassay of Human Choriogonadotropin with Magnetic Electrodes, Clin. Chem. 31/9, 1449-1452 (1985).*

* cited by examiner

SELF-ACTUATING SIGNAL PRODUCING DETECTION DEVICES AND METHODS

PRIORITY DATA AND INCORPORATION BY REFERENCE

This application claims benefit of priority to U.S. Provisional Patent Application No. 60/960,112, filed Sep. 17, 2007 and U.S. Provisional Patent Application No. 61/123,280, filed Apr. 7, 2008 which are incorporated by reference in its entirety. This application is related to a patent application filed on even date herewith naming the same inventors, U.S. application Ser. No. 12/211,992.

BACKGROUND OF THE INVENTION

Field of the Invention

In the following discussion certain subject matter will be described for background and introductory purposes. Nothing contained herein is to be construed as an "admission" of prior art. Applicant expressly reserves the right to demonstrate, should it be deemed necessary and where appropriate, that any subject matter referenced herein does not constitute prior art under the applicable statutory provisions of Title 35 of the United States Code.

The present invention relates to novel devices and methods for analyte detection. The embodiments are useful in a wide range of fields, including, inter alia, in vitro diagnostics, clinical medicine, developmental medicine, pharmaceuticals, pharmacogenomics, homeland security, military/defense, agro-chemical, industrial chemical, cosmetics, dietary supplements, genomics, toxicology, metabolomics, therapeutics, emergency response, holistic medicine, homeopathy, genetic screening, and general product quality assurance.

There continues to be an increased need and demand for new and improved detection methodologies that exhibit, for example, one or more of the following characteristics: (i) accurate, (ii) highly selective (i.e., capable of correctly discriminating between possible target molecules with low background and false results—positive or negative), (iii) high sensitivity (iv) rapid results, (v) readily adapted to targets of interest, (vi) cost effective and, optionally, (vii) capable of portable (i.e., field) use. The present invention addresses each of these demands and fulfills a long-felt and unfulfilled need in detection technology. In addition to the general demand for accurate, reliable and sensitive testing methods and devices, recent quality issues in pharmaceutical and health care related products produced in China highlight the need for improved quality assurance diagnostics. The present invention satisfies, inter alia, each of these criteria.

By way of background, the following discussion of various technologies is provided to aid in understanding the context in which the present invention was developed. The headings are not intended to be delimiting, inclusive or exclusive of any particular subject matter, but instead are employed simply to aid the reader in a contextual manner.

Related Art

This invention pertains to materials, devices, systems and methods for the detection of target substances in a larger volume. The volume, or sample, may be liquid or dry, but it is placed ultimately in a liquid test environment. The invention disclosed and claimed herein is particularly suited to the detection of targets present in extremely small concentrations, whose detection is nonetheless essential. The detection of various targets such as antibodies, spores, bacteria and the like, at an initial and low concentration, may permit the implementation of preventive or treatment strategies not available if detection is deferred until a later time. This invention has its background in a variety of established detection assays and reagents, discussed below.

An ideal detection assay would combine the versatility and selectivity of antibody recognition, speed, accuracy, sensitivity, broad applicability, the ability to multiplex and, optionally, the ability to perform such assays in "field applications" (e.g., outside of the confines of research, analytical or clinical laboratories), and/or without the need for external power supplies or instrumentation, all while overcoming the inherent deficiencies exhibited by currently known detection methods.

The present invention satisfies each of these objectives and fulfills one or more long-felt and unfulfilled needs in the field of detection technology.

SUMMARY OF THE INVENTION

The present invention provides, inter alia, detection devices and methods that exhibit increased sensitivity, are high selectivity, and can perform measurements in a rapid fashion while exhibiting little or no background. The present invention also provides embodiments of such devices and methods that are, optionally, suitable for and/or capable of functioning in "field applications" (e.g., outside of the confines of research, analytical or clinical laboratories), and/or without the need for external power supplies or instrumentation. Devices and methods for detecting one or more target agents are taught.

There exists an ever increasing demand for accurate, sensitive, and rapid biological/chemical analysis and/or assays (a subset of which are commonly referred to as "diagnostic assays"). The need for rapidity is clearly secondary to that of accuracy, sensitivity, ease of use and applicability to the particular task. The present invention provides, inter alia, detection devices and methods that exhibit increased sensitivity, high selectivity, and/or reduced background over the prior art devices and methods. The present invention also provides embodiments of such devices and methods that are, optionally, suitable for and/or capable of functioning in "field applications" (e.g., outside of the confines of research, analytical or clinical laboratories), and/or without the need for external power supplies or instrumentation. Devices and methods for detecting one or more target agents are taught.

Embodiments of the present invention are drawn to self-actuating signal-producing ("SASP") detection devices and methods that are capable of providing accurate and rapid biological and chemical analysis and diagnostic assays (collectively referred to herein as "SASP diagnostic devices and methods"). It should be understood that this term is intended to be broadly construed to include all analytic and diagnostic assays in all applicable fields of use including, inter alia, continuous monitoring of biological and disease states, in vitro diagnostics, food assays/diagnostics, cosmetic applications, agro-chemical applications, industrial chemical applications, defense related applications, homeland security related applications, etc.

Specifically, the assay system and method of this invention rely on the generation of electrons, and the resulting potential between anode and cathode, or voltage in the closed circuit between those two electrodes, as a positive signal indicating the presence, and optionally, concentration of the target of interest in the tested sample. The sample is combined with a capture moiety, which may be a nucleic acid sequence which hybridizes with the target at a given location, or an antibody specific for that target. The capture moiety is conjugated with h an enzyme that digests a substrate. The enzyme and substrate define a redox reaction pair. Digestion of the substrate, such as glucose, by the enzyme, like glucose oxidase or dehydrogenase, generates electrons in the fluid in which the target is suspended. Suspension may be facilitated, and background noise suppressed, by ensuring the target is washed and separated from all other material in the sample by adding a second capture moiety which binds to the target without interfering with the binding of the first capture moiety, which second capture moiety (typically a nucleic acid sequence or antibody different from the first) which second capture moiety is bound to a material which can be used to isolate the target, such as a magnetic bead or amino acid sequence preferentially bound by a column. Addition of the substrate to the bound target results in digestion by the bound enzyme, and generation of potential or current.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

So that the general manner in which the features, advantages and objects of the present invention are attained/attainable and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of the scope of the present invention, for the present invention may admit to and expressly includes, other embodiments not illustrated herein.

DETAILED DESCRIPTION OF THE INVENTION

This invention is described below generically and by specific example. The examples are not intended to be limiting, and do not identify limits of the invention unless specifically recited in the claims appended hereto. By the same token, the invention is described in the context of the drawings and figures described above. The figures are representative only, intended to provide the reader with specific and fine scale description of the sweeping scope of the invention. Unless so indicated by recitation in the following claims, the invention is not limited to any embodiment or device so illustrated.

Mode(s) For Carrying Out the Invention

The various embodiments will be described in detail with reference to the accompanying drawings. Wherever possible, the same reference numbers will be used throughout the drawings to refer to the same or like parts. As indicated above, this invention relies, in preferred embodiments, on the chemical reaction between and enzyme and its substrate. A typical redox pair, discussed below, is glucose oxidase and its substrate, glucose. There are a variety of ways to describe the chemical reaction that occurs between the redox enzyme and its substrate. The enzyme remains intact, but in acting upon the substrate, it typically generates electrons and "digests" or "degrades" or removes some chemical moiety from the substrate. This term is referred to herein as "acting upon." Thus, when the enzyme contacts the substrate and alters it, in the process of generating electrons or electric potential, it is described herein as an event where the enzyme "acts upon" the substrate.

Detailed Description of Certain Preferred Embodiments of the Invention

Brief Overview By Schematic

Although the invention of this patent application takes its from in a variety of specific embodiments, it can be generally characterized by reference to basic common elements. The invention employs a redox pair of reagents which liberate electrons, to provide a detectable signal when a circuit is completed. In broad outline, one of the reagents is typically an enzyme which is present only if the target is present. It is combined with the substrate for that enzyme. A variety of enzyme/substrate pairs can be used, but in general, an oxidase or dehydrogenase is used. Thus, glucose can be used with glucose oxidase or glucose dehydrogenase, lactose with lactose oxidase or dehydrogenase, etc.

Figure 1:
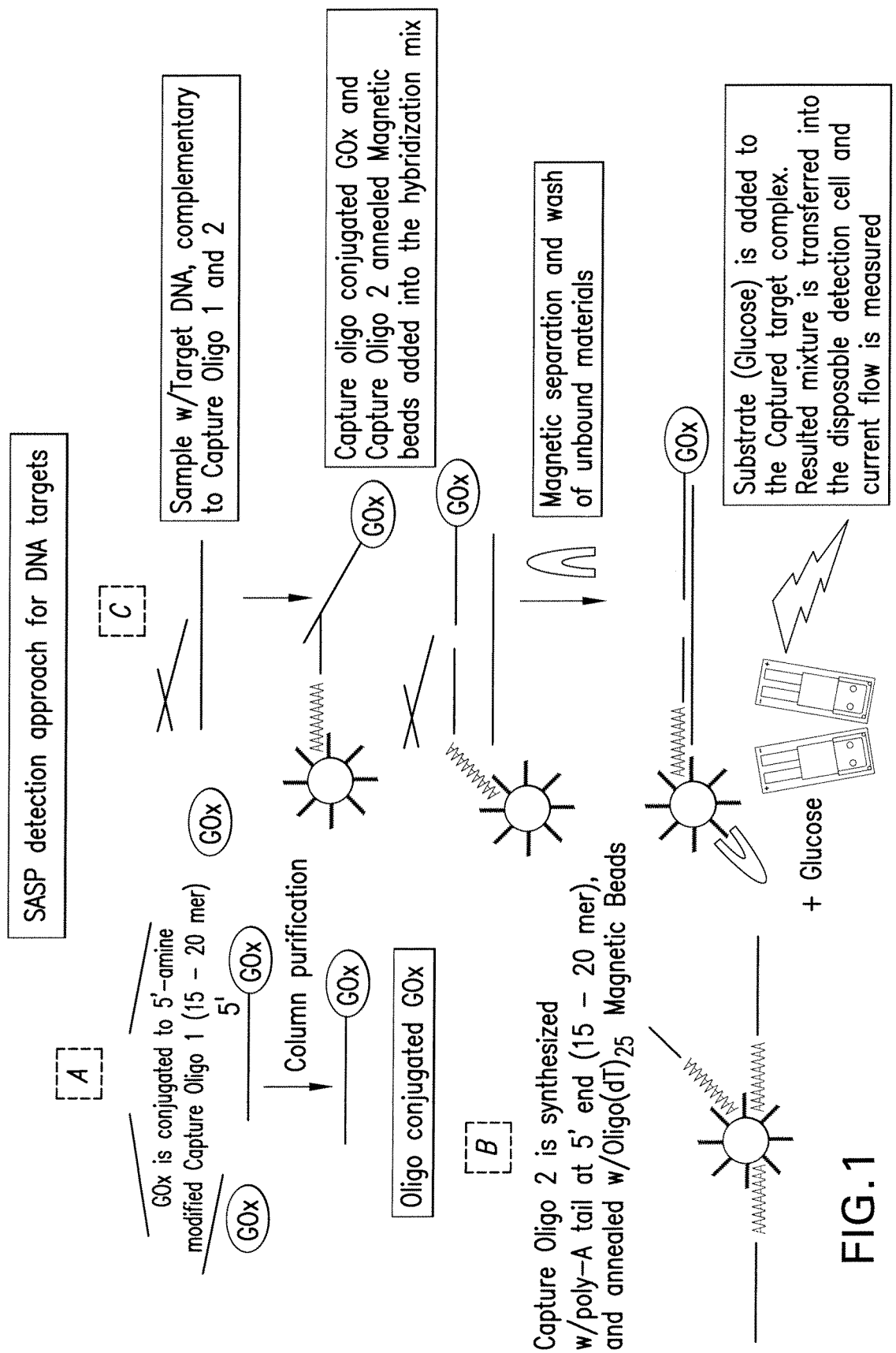
FIG. 1 is a schematic illustration of the application of this invention to detect DNA targets, such as DNA encoding a particular protein of interest.

Referring to FIG. 1 of this application, in broad outline, the assay system, methods and devices of this invention can be used to detect a wide variety of targets. One popular target is DNA of a specific sequence, or primary structure. This sequence determines what role the DNA plays, and if it encodes a protein, the identity and role of that protein. Thus, detection of target DNA is a common and important aspect of this invention. In the practice of this invention, because the detection of a signal generated by very few DNA moieties is at the heart of the invention, suppression of background noise is essential. IN the schematic of FIG. 1, background noise is reduced in part by selection of the treated agents with a magnet, the agents being repeatedly washed after being isolated. Other capture methodologies will occur to those of skill in the art, including those referenced above.

As shown, in the first or "A" stage of the invention, a member of a redox reaction pair, preferably an oxidase or dehydrogenase, is employed as a charge or electricity generation agent in the presence of the target. In the particular embodiment of the schematic, and generally, a preferred embodiment, glucose oxidase (GOx) is employed. This catalyst is coupled or conjugated to a "capture oligomer" or "Capture Oligo." The capture oligo has a sequence that will hybridize, under appropriate conditions known to those of skill in the art, to one portion of the target DNA. The conjugated GOx is purified against a column, to provide one essential reactant of the system.

A second reactant or reagent for the system of the invention is prepared in the second or B step of the method of use of the invention. This is a second capture oligomer, one which binds to a part of the target, through hybridization, which is distinct from the portion or sequence to which the first capture oligomer binds too. This second capture oligomer is in turn bound to a magnetic bead through conventional methods known to those of skill in the art. The second capture oligomer is collected by a magnet, and washed to purification. Any collection-assisting element can be used, rather than a magnetic bead. For instance, the second capture oligo could be complexed with a chemical moiety which is bound by a collection column, such a FLAG moiety. Alternatively, the second capture moiety may be complexed with an element which causes said bound target to clearly separate out of the sample when centrifuged at reasonable speeds. The critical function of the second capture moiety is that it bind to the target in such a way as to avoid inhibiting the binding of the first capture moiety bound of the enzyme, and provide a facile way of separating the bound target from the remaining material of the sample.

The third or reaction step of the invention calls for combining the two capture oligomers with the sample. These may be added simultaneously, or sequentially, depending on the desires of the practitioner. Where the capture oligomers bind the target at the same hybridization conditions, and do not otherwise compete for, or interfere with each other, in hybridizing with any target present, it may be convenient to add them together. When added to the sample under hybridization conditions, if there is any target in the sample, the target will be bound by the oligomer which presents, in this case, glucose oxidase, and the oligomer which is bound to a magnetic bead. The magnetic bead provides a simple method for purification. A magnet is applied to the vessel which holds the hybridization mixture, which may be a test tube, an ampoule, a microarray plate well, etc. The material is washed (×3). Any target bound by the second capture oligomer will be retained by the applied magnetic field.

The washed captured target is then added to a small volume loaded with the substrate for the redox catalyst, in this case, glucose. The presence of the target insures the presence of GOx, which reacts with the glucose to free electrons. Thus, the strength of signal obtained (the electricity flowing through the circuit created) is directly related to the amount of target present (each GOx molecule is tied to one target moiety). Qualification, confirming the presence of minute amounts of the target, and quantification, determining the amount of target present by the strength of the signal, can both be achieved. In absolute terms, given a 1:1 signal to target ratio (greater rations can be achieved using the turnover of the enzyme or multiple signaling moieties per molecule of target) threshold detection of 100 attomoles of target/1-3 pM concentration is well within the capabilities of the invention.

Figure 2:
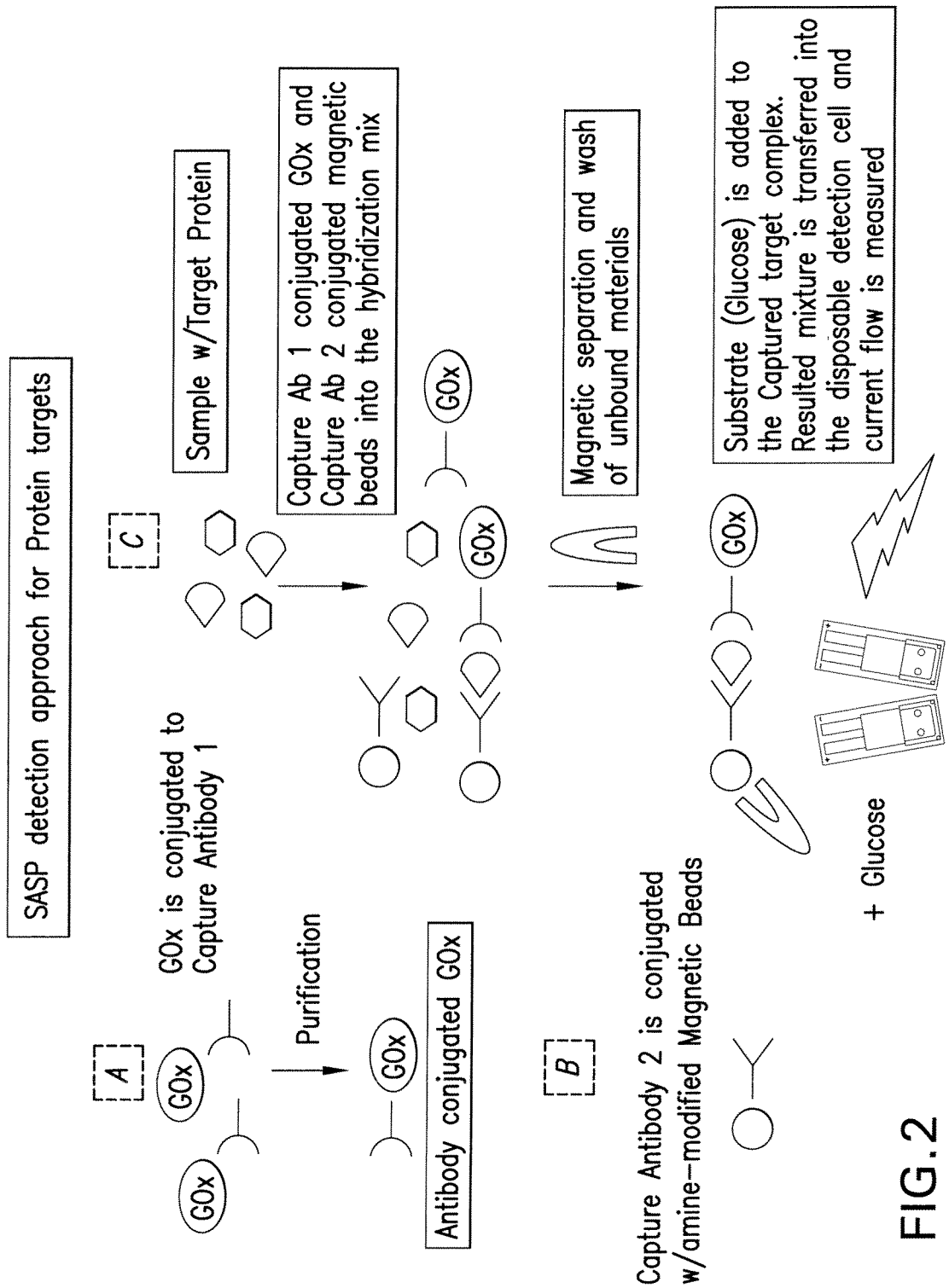
FIG. 2 is a schematic illustration of the application of this invention to detect protein targets, such as a particular protein expressed by a microorganism of interest.

Similar to the method of detecting the presence of a target DNA, as shown in FIG. 2, proteins are similarly detected. Rather than using the hybridization capabilities of DNA, use can be made of a different kind of binding moiety, antibodies. As discussed above, antibodies can be raised against a specific target—that is, they bind to that target preferentially. In the practice of the invention, the redox partner, again in this example, glucose oxidase, is conjugated to an antibody specific for the target of interest. Following conventional purification, this first capture antibody reagent is prepared.

As with the DNA target, a second capture reagent is employed. Instead of an oligomer, a second antibody is used. The antibody is conjugated to a magnetic bead in this embodiment. As before, the magnetic bead makes purification, both before and after binding to the target, easier, suppressing background noise. Other purification methods are known to those of skill in the art. The second stage or "Step B' of this process involves purification of the second capture antibody.

The $1^{st}$ and second capture antibodies bind to different portions of the target—different epitopes, to avoid competition or interference in binding. The two capture antibodies are combined, simultaneously or sequentially, with the sample. Any target present in the sample will be bound by both the $1^{st}$ capture antibody, and its given epitope, which is conjugated with a GOx moiety, and the $2^{nd}$ capture antibody, bound to a magnetic bead, and binding the target at its given epitope. The resulting antibody-target-antibody complex is separated from the detection sample by application of a magnet, which draws off any target present, the rest of the sample being washed away.

The enzyme substrate, in this case glucose, is added to the material separated off. Target bound by the antibody bound to the magnetic bead bears a glucose oxidase conjugated to the $1^{st}$ capture antibody. Addition of glucose drives the reaction, liberating electrons and driving the detectable signal. To distinguish the signal from a null signal (background) it may be desirable to delay closing the circuit for a few measurement cycles, say five minutes. This builds up a potential which, when the circuit is closed, provided a sudden strong signal which is equal to a signal obtained by constant measurement from the beginning. The "spike" of the delayed measurement is equal to the area under the curve of the constant measurement.

The above descriptions are directed to the situation of a homogenous phase, or liquid assay, that requires separation of the target from the remainder of the sample. In another preferred embodiment, the SASP technology of the present invention is used for in situ detection of target materials. For example, the redox enzyme is conjugated to a moiety such as an oligomer or antibody that is capable of selectively binding with a target specie within the sample (e.g., a tissue biopsy sample) to be tested. The sample is them placed into an appropriate detection chamber, preferably a one chambered reaction chamber wherein the cathode is painted with or otherwise separated from the anode by an appropriate polymeric membrane (i.e., Nafthion). The sample and foregoing conjugate and substrate are contacted within the reaction chamber and tested for the presence of the target material as in the preceding examples. Similarly, the presence of the target in the heterogenous sample may be the key inquiry (is there any target present). In these embodiments, a single capture moiety is used—the first capture moiety, bearing or conjugated with the redox enzyme. The second capture moiety, used to separate bound target, is not necessary.

The present invention is drawn to novel SASP detection devices and methods are capable of providing accurate and rapid biological and chemical detection, analysis and diagnostic assays (collectively referred to herein as "SASP detection devices and methods"). It should be understood that the term "SASP detection devices and methods" is intended to be broadly construed to include detection, analysis and diagnostics assays in all applicable fields of use including, inter alia, in vitro diagnostic, clinical medicine, developmental medicine, pharmaceutical, pharmacogenomics, homeland security, defense, agro-chemical, industrial chemical, cosmetic, dietary supplement, genomics, toxicology, metabolomics, therapeutics, emergency response, holistic medicine, homeopathy, genetic screening, and general product quality assurance applications.

The SASP detection devices and methods of the present invention include the ability to generate, inter alia, one or more types of signals including, but not limited to: (i) RF signals (including, but not limited to, RFID), (ii) electrical signals, (iii) photo-electronic signals, (iv) photo-reactive signals and/or (v) light emission. In preferred embodiments, the SASP devices/methods are capable of generating said signal(s) without the need for an external power source to provide all of the power necessary for signaling. In preferred embodiments, the SASP detection devices and methods of the present invention are capable of providing a signal thru the generation of electron flow derived from a catalyst, more preferred a biocatalyst and more preferred one or more of the foregoing used in conjunction and/or otherwise associated with a redox and/or redox-type reaction. In certain preferred embodiments the redox reactions include an associated biocatalyst. In certain preferred embodiments, one or more electron mediator moieties are associated with the redox reaction and/or the biocatalyst.

The SASP detection devices and methods of the present invention comprise one or more electronic circuits, which circuits are capable of generating a signal as described herein, thru, inter alia, the transfer of electrons from a catalytic reaction, preferably a biocatalytic reaction including, inter alia, an enzymatic redox system, to said circuit(s). In certain preferred embodiments, the electronic circuit is capable of generating a RF signal, and more preferably, an RFID signal. In those embodiments comprising RFID circuitry, said RF circuits can be of the passive, active and/or semi-active type, where some or all of the electrical source provided is that generated through, inter alia, a catalytic and/or redox reaction.

In certain embodiments, the enzymatic and/or redox reaction, is capable of directly charging the resonant capacitor of an RFID circuit, thereby providing the power required for RFID signal production.

The anode and/or cathode employed in certain preferred embodiments of the present invention can be formed using a conductive material, such as, for example, metal, carbon, conductive polymer, or metallic compound. Suitable conductive materials are typically non-corroding and can include, for example, gold, vitreous carbon, graphite, platinum, ruthenium dioxide, and palladium, as well as other materials known to those skilled in the art. Suitable non-conducting base materials for use with a conductive film include plastic and polymeric materials, such as, for example, polyethylene, polypropylene, polyurethanes, and polyesters. It will be understood that the anode and cathode of any particular embodiment are not necessarily made using the same materials.

The conductive material and/or the optional non-conducting base material can be, for example, non-porous, porous or microporous. For example, the conductive material and/or the optional non-conducting base material may be formed, for example, as a mesh, a reticulated structure (e.g., reticulated graphite), a microporous film, or a film that is permeable to the anode reductant and/or cathode oxidant. The surface area of the electrode can also be increased by roughening or other texturing. Preferably, the actual exposed surface area of the anode and/or cathode is larger than the macroscopic geometric surface area because the anode and/or cathode are reticulated, mesh, roughened, porous, microporous, and/or fibrous. In addition, the conductive material and/or the optional non-conducting base material can be and/or include, ion selective membrane.

Suitable electrodes can be comprised of, for example, one or more conducting and/or semi-conducting materials including, for example gold, platinum, palladium, silver, carbon, copper, indium tin oxide (ITO), and the like. For invasive analyses the electrodes are preferably constructed of bio-compatible and non-toxic materials/substances. For certain embodiments, graphite paste is a preferred material due to ease of fabrication and sufficiently large surface area. In certain embodiments, the association of the enzyme with the electrodes may be accomplished by mixing, for example, graphite powder, siloxane-ferrocene polymer and glucose oxidase and blending the resultant mixture into a paste which is subsequently packed into a well at the base of an electrode housing or applied to the electrode base plate surface. Exemplary carbon-based electrodes are discussed in U.S. Pat. No. 4,970,145, incorporated herein by reference.

The SASP detection devices and methods of the invention are preferably used without a membrane between the electrodes, thereby providing a significant benefit and ease of use and design. Less preferred embodiments can employ, as required for the particular configuration, one or more membrane and/or membrane-like materials.

In certain embodiments it is preferable that the system comprise one or more electrolytes. Where such electrolytes are employed, the electrolytes can be selected from, inter alia, those commonly used in redox reactions such as, inter alia, batteries, fuel cells, biofuel cells, etc. In general terms, the electrolytes in a system such as that employed in certain embodiments of the present invention, for example, where protons are generated on the anode, to expedite transportation of those protons to the cathode where reaction with an oxidant takes place. In a membrane containing fuel cell, a proton exchange membrane such as Nafion™ commonly serves to separate the anode from the cathode and can, optionally, serve to conduct protons from one electrode to the other. In a membrane-free fuel cell, electrolytes typically facilitate the movement of protons to the requisite electrode. Examples of electrolytes suitable for use in embodiments of the present invention, include, but are not limited to: salts, acids and bases. The electrolytes can be introduced and/or present in the form of dissolved salts, acids, or bases or, for example, may be introduced and/or present in the form of polymeric salts, acids or bases. Preferred embodiments include systems where the electrolytes, for example salts, are also capable of functioning as a buffer. Examples include, but are not limited to, those salts containing phosphates, citrates and acetates. Especially preferred are salt buffers in the pH range of about 2-7.

Representative examples of suitable enzymes include, but are not limited to glucose oxidase (GOx), lactate dehydrogenase (LDH), fructose dehydrogenase, cholin oxidase, alcohol dehydrogenase, amino acid oxidase, cytochromes, etc.

There are a variety of enzymes that are useful in association with the cathode including, for example: laccase and cytochrome C oxidase for electro-reduction of oxygen; and, peroxidases for electro-reduction of hydrogen peroxide. Similarly, useful enzymes on the anode include: hydrogenases for the electro-oxidation of hydrogen; oxidases and dehydrogenases for electrooxidation of methanol, other alcohols, glucose, lactate and other substrates; alcohol oxidase, formaldehyde dehydrogenase and formate dehydrogenase for electrooxidation of methanol; pyranose oxidase for electro-oxidation of D-glucose, L-sorbose and D-xylose; and, glucose oxidase, oligosaccharide dehydrogenase and pyrroloquinoline quinone (PQQ) glucose dehydrogenase for electro-oxidation of glucose. A non-limiting list of enzymes useful in the present invention is given in U.S. Pat. No. 6,294,281, hereby incorporated by reference.

The substrates utilized in the present invention are those capable to undergo catalytic oxidation or reduction reactions. Preferably, the substrate is usually an organic substance. Examples of representative substrates include, inter alia, sugar molecules (e.g. glucose, fructose, sucrose, mannose, etc.); hydroxy or carboxy compounds (e.g. lactate, ethanol, methanol, formic acid, etc.), ATP, carbon sources, nitrogen sources, phosphorous sources, sulfur sources, amino acids, or any other organic materials that serve are capable of functioning as a substrate for redox reactions, and more preferably, redox type enzymes.

It is particularly preferred that the enzyme systems are chosen according to the ability to oxidize a substrate which exhibits one or more of the following characteristics: (i) readily available, (ii) readily subjected to the intended redox reaction, and (iii) capable of yielding a surplus of electrons for the SASP device and/or method from said redox reaction.

In certain embodiments, the preferred enzymes are non-oxygen-specific flavo-protein or quino-protein enzymes, in particular glucose oxidase and glucose dehydrogenase. Other favo-protein enzymes include aldehyde oxidase (aldehydes), glycolate oxidase (glycolate), glutathione reductase (AND(P)H), lactate oxidase (lactate), L-amino acid oxidase (L-amino acids), lipoamide dehydrogenase (NADH), pyruvate oxidase (pyruvate), sarcosine oxidase (sarcosine), choline oxidase (choline) and xanthine oxidase (xanthine), where the substrate to which the enzyme is specific has been denoted in parenthesis.

Water, which is typically the primary mass transporting medium in many biological systems, is an electrical insulator. Although the solubility of many compounds is high in water, these compounds cannot be electrolyzed in the absence of transport of electrons through the aqueous medium. This can be accomplished by a variety of methods, including, for example, using a redox polymer, and in particular a redox hydrogel. Redox polymers generally provide for adequate transport of electrons if the redox polymer includes active redox functional groups that are mobile and can carry electrons between the analyte and the electrode. For example, a redox hydrogel typically contains a large amount of water. Water soluble reactants and products often permeate through the redox hydrogel nearly as fast as they diffuse through water. Electron conduction in the redox hydrogel is through electron exchange between polymer segments that are mobile after the polymer is hydrated.

In certain preferred embodiments, an anode redox polymer and/or cathode redox polymer are deposited on the anode and cathode, respectively. In general, the redox polymers comprise electroreducible and electrooxidizable ions, functionalities, species, or other molecules and/or moieties having redox potentials. Preferably, these redox potentials are well-defined. The redox potentials of the redox hydrogels are typically within a range at which water is neither electrooxidized or electroreduced. At neutral pH and 25° C., this range is from about (−)0.65 V to about (+)0.58 V versus the standard calomel electrode (SCE) (i.e., from about (−)0.42 V to about (+)0.81 V versus the standard hydrogen electrode (SHE)). A preferred range of the redox potential for the anode redox polymer is from about −0.65 V to about +0.05 V (SCE). A preferred range of the redox potential for the cathode redox polymer is from about +0.3 V to about +0.7 V (SCE).

In some embodiments, the preferred redox polymers include a redox species bound to a polymer which can in turn be immobilized on the working electrode. In general, redox polymers suitable for use in the invention have structures or charges that prevent or substantially reduce the diffusional loss of the redox species during the period of time that the sample is being analyzed. The bond between the redox species and the polymer may be covalent, coordinative, or ionic. Examples of useful redox polymers and methods for producing them are described in U.S. Pat. Nos. 5,262,035; 5,262,305; 5,320,725; 5,264,104; 5,264,105; 5,356,786; 5,593,852; and 5,665,222, incorporated herein by reference. Although any organic or organometallic redox species can be bound to a polymer and used as a redox polymer, preferred redox species include a transition metal compound or complex. In such embodiments, preferred transition metal compounds or complexes include osmium, ruthenium, iron, and cobalt compounds or complexes. In the preferred complexes, the transition metal is coordinatively bound to one or more ligands and covalently bound to at least one other ligand. The ligands are often mono-, di-, tri-, or tetradentate. The more preferred ligands are heterocyclic nitrogen compounds, such as, for example, pyridine and/or imidazole derivatives. For example, the multidentate ligands typically include multiple pyridine and/or imidazole rings. Alternatively, polymer-bound metallocene derivatives, such as, for example, ferrocene, can be used. An example of this type of redox polymer is poly(vinylferrocene) or a derivative of poly(vinylferrocene) functionalized to increase swelling of the redox polymer in water.

Another type of redox polymer contains an ionically-bound redox species. Typically, this type of mediator includes a charged polymer coupled to an oppositely charged redox species. Examples of this type of redox polymer include a negatively charged polymer such as Nafion® (DuPont) coupled to multiple positively charged redox species such as an osmium or ruthenium polypyridyl cations. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a multiply charged, often polyanionic, redox species bound within an oppositely charged polymer.

A variety of methods may be used to immobilize a redox polymer on an electrode surface and the embodiments of the present invention are not limited to any particular method, expressly identified herein or otherwise know to those of skill in the art. One representative method is adsorptive immobilization. This method is particularly useful for redox polymers with relatively high molecular weights. The molecular weight of a polymer may be increased, for example, by cross-linking. The polymer of the redox polymer may contain functional groups, such as, for example, hydrazide, amine, alcohol, heterocyclic nitrogen, vinyl, allyl, and carboxylic acid groups, that can be crosslinked using a crosslinking agent. These functional groups may be provided on the polymer or one or more of the copolymers. Alternatively or additionally, the functional groups may be added by a reaction, such as, for example, quaternization. One example is the quaternization of PVP with bromoethylamine groups.

Alternatively, the enzyme is immobilized in a non-conducting inorganic or organic polymeric matrix to increase the thermostablity of the enzyme. Discussion regarding immobilization of an enzyme in an inorganic polymeric matrix is found U.S. Pat. No. 5,972,199 and PCT Publication WO 98/35053, each of which is incorporated herein by reference. A sol-gel polymerization process provides a method for the preparation of an inorganic polymeric matrix (e.g., glass) by the polymerization of suitable monomers at or near room-temperature. Suitable monomers can include, for example, alkoxides and esters of metallic and semiconducting elements, with preferred metallic and semiconducting elements including Si, Al, Ti, Zr, and P. The more preferred monomers include silicon and have a silicon to oxygen ratio from about 1:2 to about 1:4.

The SASP detection devices/methods can, inter alia, be utilized in a variety of formats bending on the specific application to which it is employed. The following exemplified embodiments are intended to illustrate the invention and shall not be construed as limiting the scope of the invention in any manner.

Example I

Figure 3:
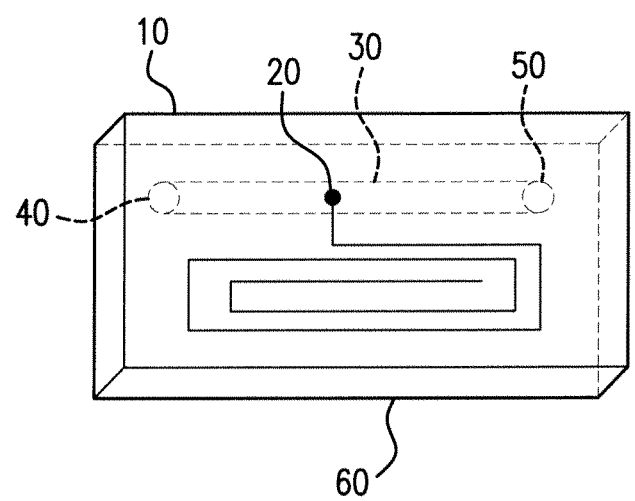
FIG. 3 depicts an embodiment of the present invention wherein a "flow through" type embodiment is employed.
Figure 4:
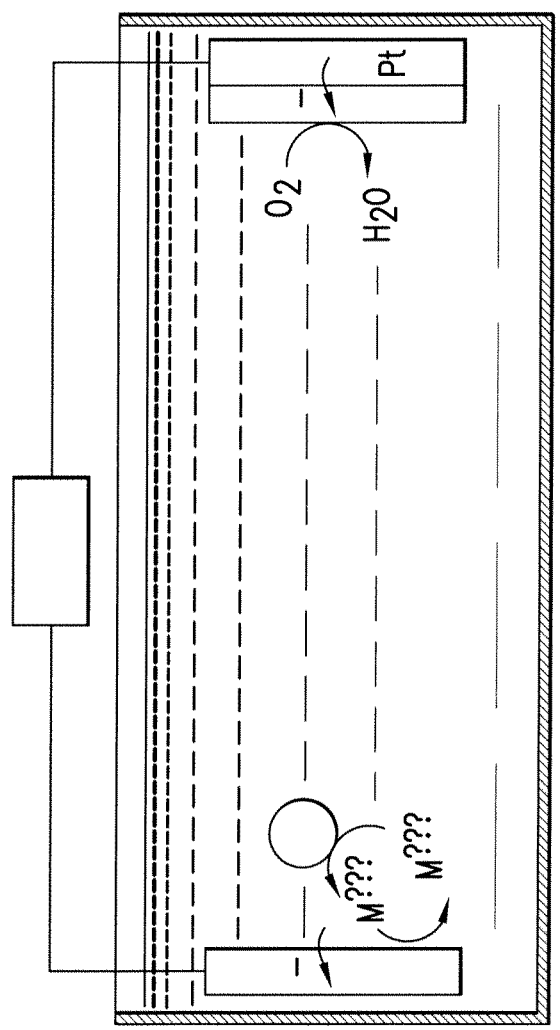
FIG. 4 depicts a biocatalysis redox electrode schematic.
Figure 5:
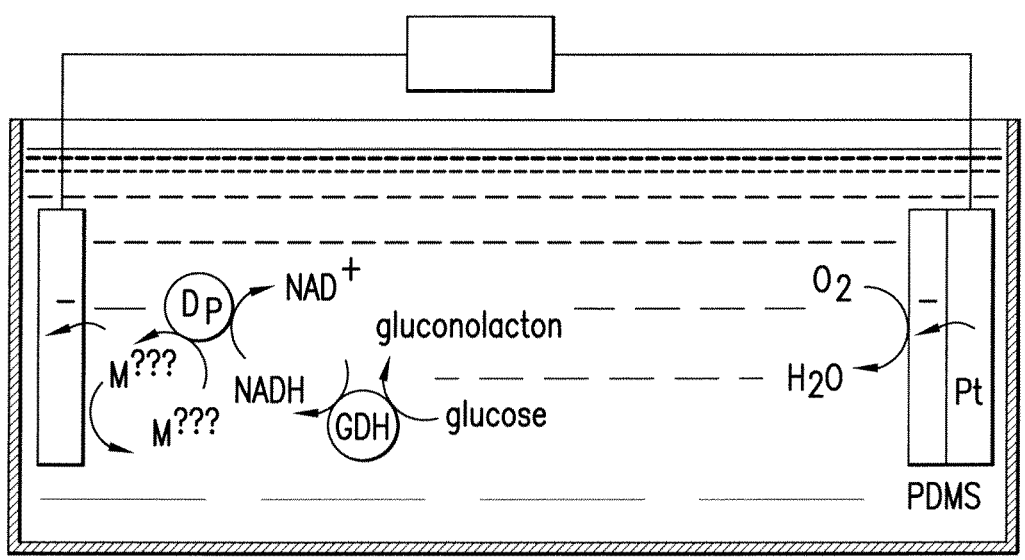
FIG. 5 depicts an alternative biocatalysis redox electrode schematic.

Reference is made to FIG. 3 which schematically depicts a SASP device, which can optionally be used in an instrument, and which employs a flow through "chip" design. It must be recognized and understood, however, that many other assemblies/formats can be fabricated, that are based on the concept of the present invention.

FIG. 3 depicts a not-to-scale representative example of a type of "flow through" type embodiment in accordance with the present invention. Liquids are able to flow from access port 40 (which is in communication with flow path 30 to access port 50 (which is also in communication with flow path 30).

Figure 6:
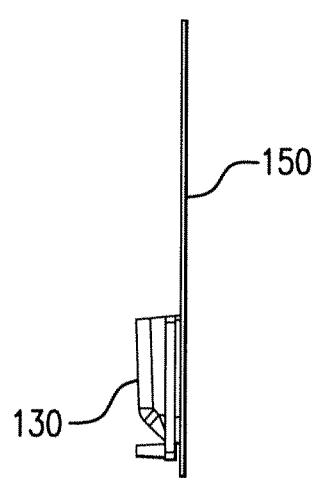
FIG. 6 depicts an electrode-provided disposable reaction chamber for a preferred embodiment of the invention in side elevation.
Figure 7:
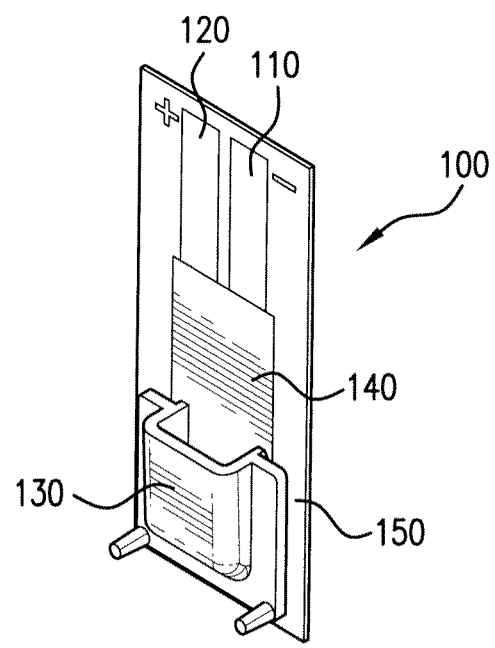
FIG. 7 depicts the reaction chamber of FIG. 6 in front elevation.

Located within flow path 30, is one or more reaction zones (20) (an example of which is representatively depicted in FIG. 6). Reaction zone(s) 20 comprise one of more electrodes, a representative non-limiting example of which are depicted in FIG. 7.

In operation, sample suspected of containing target analyte (not shown) is contacted with reagent (not shown) containing a first antibody which is conjugated to an essential element of the enymatic/redox reaction of the present invention (e.g., glucose oxidase "GOx"). Optionally, other reagents can be admixed as required. GOx conjugated antibody, which antibody is bound to target analyte is present (not shown), is introduced to chip 10 via access port 40. Sample volume traverses flow path 30, exiting via access port 50. During such traversing, sample volume traverses reaction zone 20. The number of reaction zones (20) is dependent upon the test(s) to be performed and the application to which such test(s) is applied and can vary as necessary. The number of reaction zones can be within a range of 1-1000, preferably between 1-100, more preferably between 1-50, more preferably between 1-25, more preferably between 2-20 and most preferably between 1-10 or 2-10 or alternatively, 1-5 or 2-5.

On reaching reaction zone(s) 20, any target analyte molecule present in the sample should be captured by a second antibody, so "immobilizing" the labeled "sandwich" so produced. This sandwich immobilization in zone 20, thereby positions the enzyme in close proximity to the electrode(s) within zone 20, thereby enabling the redox biocatalysis and generation of electron flow, which in turn powers, directly or indirectly, a signaling event in the presence of enzyme substrate (not shown). Enzyme substrate (not shown) is added, preferably via access port 40.

In contrast to, for example, the glucose biosensors and other diagnostic devices of the prior art, the sandwich capture of the enzyme/redox element in reaction zone 20 is expressly not for the purpose of detecting the substrate of the captured enzyme. Rather, the localization of, in this example, the antibody-conjugated GOx, does not detect the presence or amount of glucose, but instead, is used as an in situ generated biofuel cell, which when glucose is added (e.g., via access port 40), the enzyme redox system is capable of producing electron flow and thereby, directly or indirectly, present a system capable of generating a signal in accordance with the various embodiments of the present invention. Thus, absent the addition of the enzyme substrate, the signaling event cannot occur (or alternatively, occurs at a sufficiently low level, relative to when the substrate is present, so as to allow a distinguishable signal).

In a preferred operation, the sample containing (or suspected of containing) the target analyte, is suspended in an appropriate buffer for the particular system employed, and introduced (manually or automated means) into the flow through chip. The substrate is captured by a capture moiety(ies) associated with said RF circuitry. Suitable capture moieties include any moiety capable of the selective capture of the target/enzyme system in a manner to localize the reaction in the proximity of the RF circuit/electrode complex. Preferred capture moieties include antibodies, and more preferably monoclonal antibodies. The capture complex is preferably designed to associate the target analyte with the enzyme complex (or component thereof) with the electrode/circuit complex In a preferred embodiment the flow through chip is optionally flushed to remove unbound reagents. The specific substrate for the enzyme/redox complex is then added to the flow through chip port (50), so as to allow for the catalytic generation of electrons through the catalyst/redox reaction. Thus, where the target analyte is present, the resulting complex will include all necessary catalyst/redox system components in association with the electrode/RF circuit complex and, thereby result in the generation of a detectable RF signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

Example II

In contrast to, for example, the glucose biosensors and other diagnostic devices of the prior art, the sandwich capture of the enzyme/redox element in a reaction zone is expressly not for the purpose of detecting the substrate of the captured enzyme. Rather, the localization of, in this example, the antibody-conjugated GOx, does not detect the presence or amount of glucose, but instead, is used as an in situ generated biofuel cell, which when glucose is added the enzyme redox system is capable of producing electron flow and thereby, directly or ondirectly, present a system capable of generating a signal in accordance with the various embodiments of the present invention. Thus, absent the addition of the enzyme substrate, the signaling event cannot occur (or alternatively, occurs at a sufficiently low level, relative to when the substrate is present, so as to allow a distinguishable signal).

In a preferred embodiment, the reaction zone comprises electrodes associated with RF circuitry in a manner suitable to allow the transfer of electrons from said the reduction/oxidation of the substrate by the redox enzyme system, such that the flow of electrons functions to provide the poser required by the RF circuitry to produce a detectable signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

In a preferred embodiment, the RF signal is detected by a hand held detector. In a more preferred embodiment, the RF signal is detected by a battery powered hand held detector. In a more preferred embodiment, the RF signal is detected by a wristwatch-styled detector.

Example III

In a preferred operation, the sample containing (or suspected of containing) the target analyte, is suspended in an appropriate buffer for the particular system employed, and introduced (manually or automated means) into the flow through the device body. The substrate is captured within reaction zone by a capture moiety(ies) associated, directly or indirectly, with electrodes which in turn are associated, directly or indirectly, with an electronic circuit (e.g., RF circuitry). Suitable capture moieties include any moiety capable of the selective capture of the target/enzyme system in a manner to localize the reaction in the proximity of the RF circuit/electrode complex. Preferred capture moieties include nucleic acids and/or antibodies, and more preferably monoclonal antibodies. The capture complex is preferably designed to associate the target analyte with the enzyme complex (or component thereof) with the electrode/circuit complex.

In a preferred embodiment the flow through chip is optionally flushed to remove unbound reagents. The specific substrate for the enzyme/redox complex is then added passed thru the device, so as to allow for the catalytic generation of electrons through the catalyst/redox reaction. Thus, where the target analyte is present, the resulting complex will include all necessary catalyst/redox system components in association with the electrode/RF circuit complex and, thereby result in the generation of a detectable RF signal.

In a preferred embodiment, the enzyme/redox substrate is provided in molar excess. In a more preferred embodiment, the substrate is provided in a 10 fold molar excess. In a more preferred embodiment, the substrate is provided in a 100 fold molar excess. In a more preferred embodiment, the substrate is provided in a 1,000 fold molar excess. In a more preferred embodiment, the substrate is provided in a 10,000 fold molar excess. In a more preferred embodiment, the substrate is provided in a 100,000 fold molar excess. In a more preferred embodiment, the substrate is provided in a 1,000,000 fold molar excess. In a more preferred embodiment, the substrate is provided in an amount in excess of a 1,000,000 fold molar excess.

Example IV

In this particular embodiment, an oxidation reaction of glucose proceeds at an anode, and a reduction reaction of oxygen proceeds at a cathode. An enzyme required for glucose oxidation (glucose oxidase (GOx), in this case) and a mediator act at the anode to take electrons discharged from the oxidation reaction of glucose out of a system. The GOx is associated with the anode through the SASP reaction at the reactive zone (see, e.g., FIG. 1 at element 20). The electrons are taken out of the system through the depicted circuit, which circuit can produce a variety of signals in accordance with the present invention, including, inter alia, a RF signal. Glucose is used as a "fuel" in this example.

Example V

In this particular embodiment, an oxidation reaction of glucose proceeds at an anode, and a reduction reaction of oxygen proceeds at a cathode. An enzyme required for glucose oxidation (glucose dehydrogenase (GDH), in this case), a coenzyme (NADH), diphorase, and a mediator, act at the anode to take electrons discharged from the oxidation reaction of glucose out of a system. The GDH is associated with the anode through the SASP reaction at the reactive zone (see, e.g., FIG. 1 at element 20). The electrons are taken out of the system through the depicted circuit, which circuit can produce a variety of signals in accordance with the present invention, including, inter alia, a RF signal. Glucose is used as a "fuel" in this example.

Figure 8:
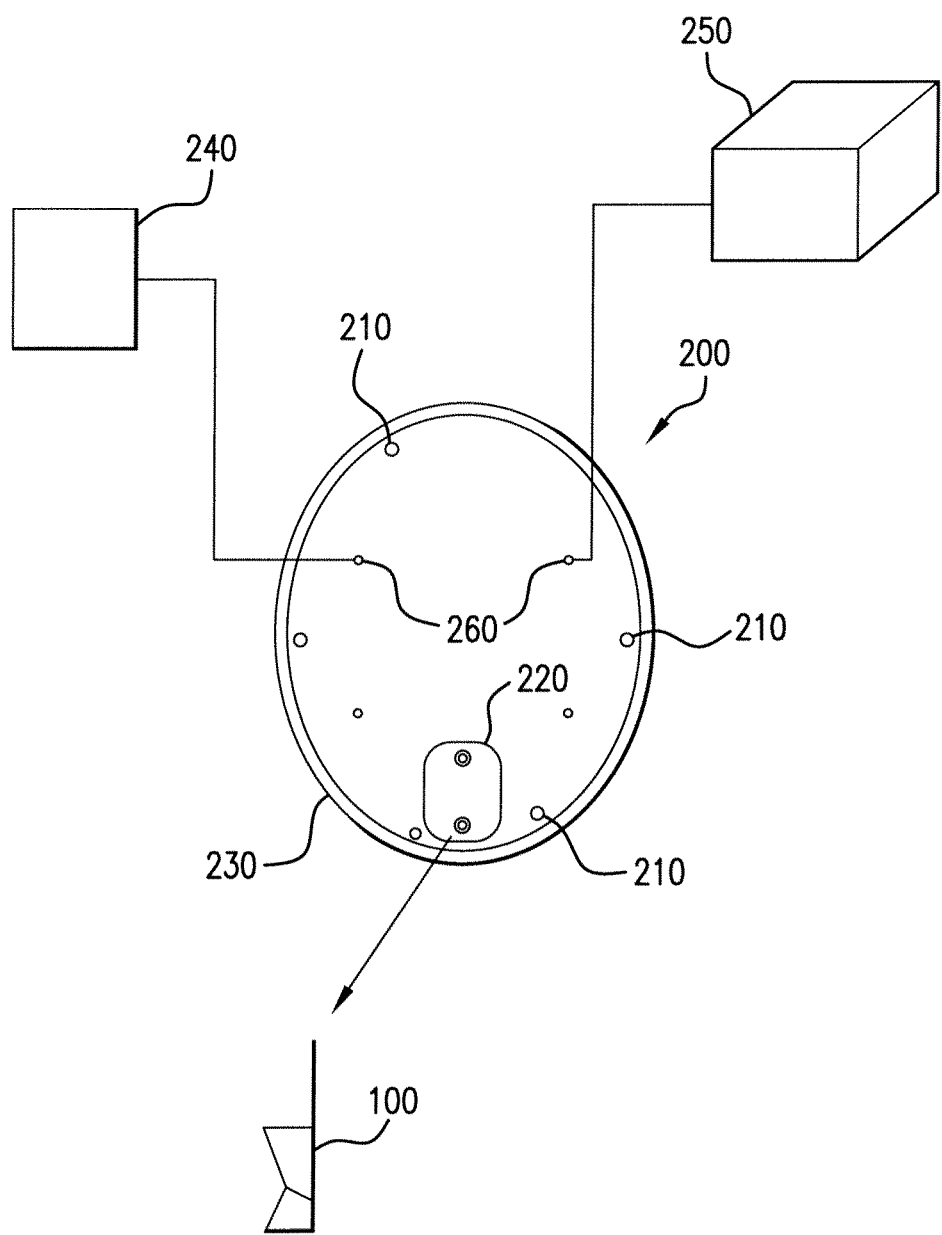
FIG. 8 depicts a field deployable device for receiving a reaction chamber cartridge and detecting electric potential developed between the electrodes thereof in bottom elevation.
Figure 9:
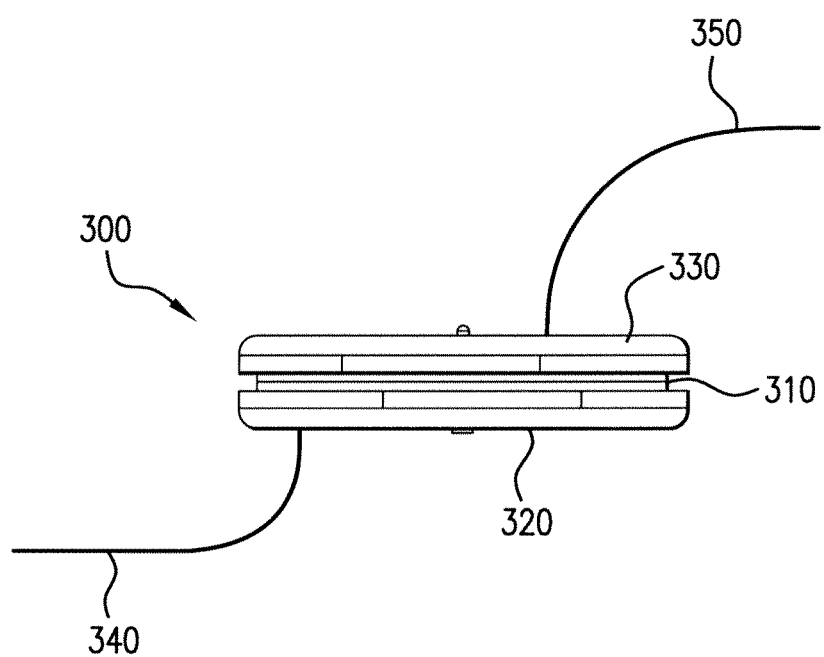
FIG. 9 depicts a field deployable device for measuring potential developed across electrodes of a disposable reaction chamber from side elevation.

At a preferred anode of the SASP devices and methods of the present invention, including, for example, the systems of FIGS. 8 and 9, one or more sugars, alcohols, and/or carboxylic acids, typically found in the biological system, are electrooxidized. Preferred anode enzymes for the electrooxidation of the anode reductant include, for example, glucose dehydrogenase, glucose oxidase, galactose oxidase, fructose dehydrogenase, quinohemoprotein alcohol dehydrogenase, pyranose oxidase, oligosaccharide dehydrogenase, and lactate oxidase.

One embodiment of the anode is formed using a high surface area graphite fiber/carbon black electrode using polypropylene or polytetrafluoroethylene as a binder. The anode redox polymer and anode enzyme are then disposed on the anode.

The anode potential can be limited by the (a) redox potential of the anode enzyme, (b) the concentration of the anode reductant at the anode, and (c) the redox potential of the anode redox polymer. Reported redox potentials for known anode enzymes range from about −0.4 V to about −0.5 V versus the standard calomel electrode (SCE). Typically, the preferred anode redox polymers have a redox potential that is at least about 0.1 V positive of the redox potential of the anode enzyme. Thus, the preferred anode redox polymer can have a redox potential of, for example, about −0.3 V to −0.4 V (SCE), however, the potential of the anode redox polymer may be higher or lower depending, at least in part, on the redox potential of the anode redox enzyme.

Example VI

Reference may be had to FIGS. 6 and 7, which show, from side elevation and front elevation, together, an exemplary disposable reaction chamber cartridge of this invention. Bearing in mind that a specific feature of this invention is the ability to employ it, as a self powered device, in the field, the use of disposable cartridges or similar low cost, hardy reaction chambers becomes important. As shown in FIG. 6, the reaction chamber is mounted on a flange 150, to which is attached a reaction chamber containment area 130. The containment area, which, together with the front surface of flange 150, defines the reaction chamber, is conventionally made of molded or extruded plastic at low cost.

As more fully shown in FIG. 7, the reaction chamber defined by enclosure 130 and mounting flange 150 is of a small volume. An important aspect of this invention is the ability to test small volumes of sample and target, and generate a detectable signal. Cathode 110 and anode 120 are painted onto the surface of flange 150, or otherwise mounted hereon, and extend into the reaction chamber. They may be protected by membrane 140. In a preferred embodiment, cathode 110 is covered by a membrane that may be sprayed or painted on, such as one prepared from a proton exchange membrane, like Nafion™.

Example VII

In many embodiments of this invention, the disposable reaction chamber of FIGS. 6 and 7 is desirably read in the field, where the sample is obtained, and where the signal reflecting the presence and amount of target is taken. For these purposes, a self-powered device, containing the necessary hardware and provided with appropriate software may be deployed, designed to receive the disposable reaction chamber of FIGS. 6 and 7, such as that shown from the underside in FIG. 8. This device 200 is made of rugged plastic, and connected through a cap of similar material (330 of FIG. 9) which together harbor and protect the necessary hardware, software and firmware, including the meter or sensing device to detect potential or current flow between cathode 110 and anode 120. To this end, the bottom half of the detection device 200 is secured through holding devices (screws, bolts, rivets, etc.) to top 330 illustrated in FIG. 9. As shown, the device 200 is equipped with ports 260 from which leads may be connected to various auxiliary devices, such as RFID device 240, or computer (laptop or iTouch™ or similar PDA or mobile phone) 250. The signal, which may be read directly from a meter provided in device 200, may be stored in or broadcast to distant locations via the auxiliary devices.

The device 200 is provided with a receptacle or opening 220 intended to receive disposable reaction chamber 100. As shown, the receptacle or slot is provided with hard wired electrical contacts so as to receive current flow from cathode 110 and anode 120. These may be run to a meter or gap potential measurement device, or as noted, a more sophisticated device, such as a computer, or a data storage means which may subsequently be accessed for the signals detected, or may transmit the signal and associated data, may be connected through simple electronic connections, such as a USB cable.

The complete field deployable device for receiving, measuring and sending the signal upon addition of the substrate to the reaction chamber is illustrated in FIG. 9, where the device is indicated at 300. The base, with cartridge inserted, at 320, is secured, as indicated, to a damage resistant top 330. These sandwich and protect the interior of the device, including the wiring, software and hardware necessary to detect the potential as a signal, generally indicated at 310. Leads may extend from the device, 340 and 350, for interconnection with auxiliary devices.

Example VIII

In one embodiment, the cathode reduces gaseous $O_2$ that is typically dissolved in the biological fluid or originating from the air. In another embodiment of the fuel cell, hydrogen peroxide is formed in a non-enzyme-catalyzed electrode reaction or in an enzyme-catalyzed reaction on or off the cathode and then the hydrogen peroxide is electroreduced at the cathode. Preferred cathode enzymes for the reduction of $O_2$ and $H_2O_2$ include, for example, tyrosinase, horseradish peroxidase, soybean peroxidase, other peroxidases, laccases, and/or cytochrome C peroxidases.

One embodiment of the cathode includes a porous membrane formed over at least a portion of cathode. The porous membrane has an $O_2$ and/or $H_2O_2$ permeable, hydrophobic outer surface and an $O_2$ and/or $H_2O_2$ permeable hydrophilic inner surface. In another embodiment, the cathode includes an outer layer of a hydrophobically modified porous silicate carbon composite, formed of an alkyltrialkoxysilane precursor, and carbon black. The inner layer is a hydrophilic silica-carbon composite. In another embodiment, the electrode is a microporous Teflon PTFE bound acetylene/carbon black electrode. The inner surface is plasma processed to make it hydrophilic. The redox polymer and enzyme are deposited on the inner surface of the cathode. When the cathode is exposed to $O_2$ originating in blood or a body fluid, the cathode may only include hydrophilic surfaces in contact with the $O_2$ transporting biological fluid.

The cathode potential can be limited by the (a) redox potential of the cathode enzyme, (b) the concentration of the cathode oxidant at the cathode, and (c) the redox potential of the cathode redox polymer. Reported redox potentials for known $O_2$ reducing enzymes range from about +0.3 V to about +0.6 V versus the standard calomel electrode (SCE). Typically, the preferred cathode redox polymer has a redox potential that is at least about 0.1 V negative of the redox potential of the enzyme. Thus, the preferred redox polymer has redox potential of, for example, about +0.4 to +0.5 V (SCE), however, the potential of the cathode redox polymer may be higher or lower depending, at least in part, on the redox potential of the cathode redox enzyme.

For osmium complexes used as the cathode redox polymer, typically, at least four, usually, at least five, and, often, all six of the possible coordination sites of the central osmium atom are occupied by nitrogen atoms. Alternatively, for complexes of ruthenium used as the cathode redox polymer, typically, four or fewer, and, usually, three or fewer of the Example IX Capture 2 oligonucleotide #100003_15_amino (5' amino modified 15 nucleotides long) [SEQ ID NO.: 1] is synthesized using standard phosphoramidite chemistry (TriLink BioTechnologies, Inc. San Diego, Calif.). 5'-AGGATGACACCTAGA-3'.

The oligonucleotide is then purified using NAP-5 column (0.1M/0.15M buffer of $NaHCO_3$/NaCl, pH 8.3). 0.2 ml of 100 uM water solution of oligonucleotide #100003_15_amino is loaded on a column. After 0.3 ml push 0.8 ml of eluant is collected and quantified. Based on $A_{260}$ reading more than 90% of recovery is observed. Purified oligonucleotide subsequently is chemically modified using Succinimidyl 4-formylbenzoate (C6-SFB). 790 ul of purified oligonucleotide and 36 ul of C6-SFB (20 mM in DMF) are mixed (1:40 ratio) and incubated at room temperature for 2 hrs.

Reaction product is cleaned up using 5 ml HiTrap (GE) desalting column and 1.5 ml eluant is collected. Based on $A_{260}$ reading more than 80% recovery of oligonucleotide-C6-SFB is observed.

A Glucose Oxidase from *Aspergillus niger* (Fluka, 49180) is purified using NAP-5 column (1×PBS buffer, pH 7.2).

0.25 ml of Glucose Oxidase (5 mg/ml) is loaded on a column. After 0.25 ml push 1 ml of eluant is collected and quantified. Based on $A_{280}$ reading 1.25 mg/ml (7.8 uM) Glucose Oxidase recovery is observed.

Purified Glucose Oxidase subsequently is chemically modified using Succinimidyl 4-hydrazinonicotinate acetone hydrazone (C6-SANH). 950 ul of 7.8 uM of Glucose Oxidase and 10.4 ul of C6-SANH (10 mM in DMF) are mixed (1:20 ratio) and incubated at room temperature for 30 min. Reaction product is cleaned up using 5 ml HiTrap (GE) desalting column and 1.25 ml eluant is collected. BCA/BSA (BCA assay from Pierce, cat #23225/23227; Bradford assay from Pierce, cat #23236) assay is used to determine the concentration of recovered Glucose Oxidase-C6-SANH (typically ~1 mg/ml, yield more than 95%).

The conjugation of Glucose Oxidase and oligonucleotide is typically achieved by mixing the 1010 ul of Glucose Oxidase-C6-SANH and 750 ul of oligonucleotide-C6-SFB in a molar ratio 1:2 and incubated overnight at room temperature. The resulting conjugates are analyzed on TBE/UREA gel, and purified using MiniQ FPLC. Standard gradient approach is utilized using MiniQ 4.6/50 PE column (GE Healthcare, cat #17-5177-01), 0.25 ml/min flow rate, detection at 280 nm. buffer A: 20 mM Tris/HCl, pH 8.1, buffer B: 20 mM Tris/HCl, NaCl 1M, pH 8.1. BCA/BSA assay is used to determine the concentration of recovered Glucose Oxidase-capture 2 oligonucleotide conjugate (~3 ml of eluant, 0.15 mg/ml).

Example X

Preparation of DNA-Enzyme Conjugates

Capture 2 oligonucleotide #100003_15_amino (5' amino modified 15 nucleotides long) [SEQ ID NO.: 1] is synthesized using standard phosphoramidite chemistry (TriLink BioTechnologies, Inc. San Diego, Calif.). 5'-AG-GATGACACCTAGA-3'.

The oligonucleotide is then purified using NAP-5 column (0.1M/0.15M buffer of $NaHCO_3$/NaCl, pH 8.3). 0.2 ml of 100 uM water solution of oligonucleotide #100003_15_amino is loaded on a column. After 0.3 ml push 0.8 ml of eluant is collected and quantified. Based on $A_{260}$ reading more than 90% of recovery is observed. Purified oligonucleotide subsequently is conjugated with Glucose Oxidase using a commercially available Lightning-Link Glucose Oxidase Congugation Kit (Innova Biosciences Ltd, Cambridge, UK. Cat #706-0010) following the manufacturers protocol with some modifications. Briefly, 4 ul of modifier is added to 40 ul of amino modified oligo (50 uM in water). Resulted 44 ul of solution is added into ½ vial of LL-Gox and incubated overnight at room temperature in dark. After incubation 5 ul of quencher is added to the reaction mixture and incubated for 30 min at room temperature in dark.

The resulting conjugate subsequently is purified via Micron YM-100 spin column (Millipore, USA) to remove an access of amino modified oligonucleotide. Briefly, 50 ul of conjugate is loaded into the column and centrifuge at 8000 rpm for 8 min. Flow through is discarded. 200 ul of 1× (50 mM) PBS (50 mM, pH 7.5) is added to a column and centrifuge at 8000 rpm for 8 min. Flow through is discarded. 50 ul of 1×PBS (50 mM, pH 7.5) is added to a column, carefully mixed using a vortex for a few seconds and centrifuge at 2000 rpm for 2 min. 50 ul of purified capture 1 oligonucleotide. Enzyme conjugate is collected and saved at 4° C. for future use.

Example XI

Preparation of DNA Immobilized-Oligo $(dT)_{25}$ Magnetic Beads

Capture 1 oligonucleotide #100003_19_polyA (36 nucleotides long) [SEQ ID NO.: 2] is synthesized using standard phosphoramidite chemistry (TriLink BioTechnologies, Inc. San Diego, Calif.). 5'-GTGATCGG-GAGTGTGTCCAAAAAAAAAAAAAAAAAA-3'.

The oligonucleotide is then purified using NAP-5 column (0.1M/0.15M buffer of $NaHCO_3$/NaCl, pH 8.3). 0.2 ml of 100 uM water solution of oligonucleotide #100003_15_amino is loaded on a column. After 0.3 ml push 0.8 ml of eluant is collected and quantified. Based on $A_{260}$ reading more than 90% of recovery is observed. Purified oligonucleotide subsequently is annealed with Oligo $(dT)_{25}$ magnetic beads (Dynabeads Oligo $(dT)_{25}$, Invitrogen Corporation, Carlsbad, Calif. Cat #610). Briefly, 30 ul of magnetic beads suspension is washed twice with 1× Binding buffer (20 mM Tris-HCl, pH 7.5, 1.0M LiCl, 2 mM EDTA). Each time magnetic beads are separated using Magnetic Particle Concentrator (Dynal MPC™-S, Invitrogen Corporation, Carlsbad, Calif. Cat #120.20D).

After final wash the beads are resuspended in 30 ul of Binding buffer and mixed with 2.6 ul of capture 1 oligonucleotide #100003_19_polyA (26 pmole). Final reaction volume is brought to 45 ul final volume by adding water and 0.01% Tween 20, and incubated at room temperature with continuous rotation (~30-45 min). After incubation annealed magnetic beads are separated using Magnetic Particle Concentrator, supernatant is discarded. Magnetic beads subsequently are washed (3 times) with Washing buffer B (10 mM Tris-HCl, pH 7.5, 0.15M LiCl, 1 mM EDTA), washed once with Storage Buffer Oligo $(dT)_{25}$ (250 mM Tris-HCl, pH 7.5, 20 mM EDTA, 0.1% Tween-20, 0.02% $NaN_3$), resuspended in 30 ul of Storage Buffer Oligo $(dT)_{25}$, and kept at 4° C. for future use.

Example XII

Binding of Target Agent and Removal of Excess DNA-Enzyme Conjugate (Model System Study)

A DNA Target Agent, oligonucleotide 100003_39 (39 nucleotides long) [SEQ ID NO.: 3] was synthesized using standard phosphoramidite chemistry (TriLink BioTechnologies, Inc. San Diego, Calif.) and is purified as described in Example XI. 5'-TGGACACACTCCCGATCACCAC-GATCTAGGTGTCATCCT-3'.

Capture 2 oligonucleotide #100003_15_amino is conjugated to a Glucose Oxidase from *Aspergillus niger* (Fluka, 49180) according to the procedure for conjugation described supra. Typically 0.15 mg/ml of the conjugate is obtained.

In parallel Capture 1 oligonucleotide immobilized-Oligo $(dT)_{25}$ magnetic beads is prepared according to the procedure for annealing described above.

To reconstitute a model system 100 fmol of Target Agent, oligonucleotide 100003_39, is spiked into 1 ug of Human Genomic DNA (Clontech, Palo Alto, Calif. Cat #636401)

along with 0.5 pmol of Capture 2 oligonucleotide-Glucose oxidase conjugate. Total reaction volume is 30 ul (6×SSPE, 0.01% Tween 20). The resulting reaction mixture is transferred into the tube containing 0.5 pmol of washed, dry Capture 1 oligonucleotide immobilized-Oligo $(dT)_{25}$ magnetic beads and gently mixed. Hybridization is carried at room temperature with continuous rotation for 1 hr.

Unbound Capture 2 oligonucleotide-Glucose oxidase conjugate is removed by washing (3 times) with 6×SSPE (0.9M NaCl, 60 mM $NaH_2PO_4$, 6 mM EDTA). Each time magnetic beads are separated using Magnetic Particle Concentrator (Dynal MPC™-S, Invitrogen Corporation, Carlsbad, Calif. Cat #120.20D). After the last wash the supernatant is carefully removed, remaining magnetic beads are resuspended in 10 ul of 2M Potassium Phosphate Buffer (pH 6.0) and kept at 4° C.

The Target Agent bound Capture 2 oligonucleotide-Glucose oxidase conjugate remains on the magnetic beads and is available for detection. In parallel, as a negative control, similar reaction is set up with no Target Agent spiked into 1 ug of Human Genomic DNA.

Example XIII

Detection of DNA Target Agent Bound Magnetic Beads (Model System Study)

A DNA Target Agent bound magnetic beads is prepared according to the capture procedure described above. Resulted 10 ul of Target Agent bound magnetic beads is washed (2 times) with 100 ul of 2M Potassium Phosphate Buffer (pH 6.0).

Each time magnetic beads are separated using Magnetic Particle Concentrator (Dynal MPC™-S, Invitrogen Corporation, Carlsbad, Calif. Cat #120.20D). After the last was the supernatant is carefully removed, remaining magnetic beads are resuspended in 2-5 ul of buffer containing 2M Potassium Phosphate Buffer (pH 6.0), 0.1 mM DCPIP (2,6-Dichloroindophelol, 0.1 ug/ul BSA).

In parallel a Detection Cell is assembled. Detection Cell contains 2 reaction chambers (anode and cathode reaction chambers) separated by NAFION Membrane N-117 (FuelCellStore, San Diego, USA). Each reaction chamber has gold electrode inserted in it. Gold electrodes are connected to Fluke 289 True-RMS Industrial Logging Multimeter with TrendCapture (Fluke, Everett, Wash., USA) to take potentiometric or amperometric measurements.

20 ul of Working Buffer (2M Potassium Phosphate Buffer (pH 6.0), 0.1 mM DCPIP (2,6-Dichloroindophelol)) is added to each reaction chamber. 1 ul of Target bound magnetic beads is mixed with 1 ul of 1M glucose and transferred into anode reaction chamber. Potentiometric measurements are taken continuously or every 5 minutes of interval. Presence of the DNA Target Agent is detected by measurements of increasing potential (1-55 mV range).

During the measurements of the negative control reaction no potential is detected.

Example XIV

Preparation of Antibody-Enzyme Conjugates

Capture Antibody 2, an anti-Mouse α-Human IL-8 Monoclonal Antibody (for ICC, BD Pharmingen cat #550419) is purified using NAP-5 column (0.1M/0.15M buffer of $NaHCO_3$/NaCl, pH 8.3), 0.5 ml loaded, 0.1 ml is pushed and 0.7 ml collected. Based on $A_{280}$ reading 0.45 mg/ml Mouse α-Human IL-8 Monoclonal Antibody recovery is observed.

Purified Capture Antibody 2 subsequently is chemically modified using Succinimidyl 4-formylbenzoate (C6-SFB). 660 ul of purified antibody and 30 ul of C6-SFB (20 mM in DMF) are mixed (1:40 ratio) and incubated at room temperature for 2 hrs. Reaction product is cleaned up using 5 ml HiTrap (GE) desalting column and 1.5 ml eluant is collected. Based on $A_{260}$ reading more than 80% recovery of Capture Antibody 2—C6-SFB is observed.

A Glucose Oxidase from *Aspergillus niger* (Fluka, 49180) is purified using NAP-5 column (1×PBS buffer, pH 7.2). 0.25 ml of Glucose Oxidase (5 mg/ml) is loaded on a column. After 0.25 ml push 1 ml of eluant is collected and quantified. Based on $A_{280}$ reading 1.25 mg/ml (7.8 uM) Glucose Oxidase recovery is observed.

Purified Glucose Oxidase subsequently is chemically modified using Succinimidyl 4-hydrazinonicotionate acetone hydrazone (C6-SANH). 950 ul of 7.8 uM of Glucose Oxidase and 10.4 ul of C6-SANH (10 mM in DMF) are mixed (1:20 ratio) and incubated at room temperature for 30 min. Reaction product is cleaned up using 5 ml HiTrap (GE) desalting column and 1.25 ml eluant is collected. BCA/BSA (BCA assay from Pierce, cat #23225/23227; Bradford assay from Pierce, cat #23236) assay is used to determine the concentration of recovered Glucose Oxidase-C6-SANH (typically ~1 mg/ml).

The conjugation of Glucose Oxidase and Capture Antibody 2 is typically achieved by mixing the 500 ul of Glucose Oxidase-C6-SANH and 750 ul of Capture Antibody 2-C6-SFB in a molar ratio 3:1 and incubated overnight at room temperature. The resulting conjugates are analyzed on TBE/UREA gel, and purified using MiniQ FPLC.

Standard gradient approach is utilized using MiniQ 4.6/50 PE column (GE Healtcare, cat #17-5177-01), 0.25 ml/min flow rate, detection at 280 nm. buffer A: 20 mM Tris/HCl, pH 8.1, buffer B: 20 mM Tris/HCl, NaCl 1M, pH 8.1. BCA/BSA assay is used to determine the concentration of recovered Glucose Oxidase-Capture Antibody 2 (~3 ml of eluant, 0.1 mg/ml).

Example XV

Preparation of Antibody Immobilized Magnetic Beads

Capture Antibody 1, an anti-Mouseα-Human IL-8 Monoclonal Antibody (ELISA capture, BD Pharmingen cat #554716) is purified using NAP-5 column (0.1M/0.15M buffer of $NaHCO_3$/NaCl, pH 8.3), 0.5 ml loaded, 0.1 ml is pushed and 0.7 ml collected. Based on $A_{280}$ reading 0.45 mg/ml Mouse α-Human IL-8 Monoclonal Antibody recovery is observed.

In parallel primary amino-derivatized magnetic beads (Dynabeads® M-270 Amine, Invitrogen Corporation, Carlsbad, Calif. Cat #610) is activated with water soluble homobifunctional NHS (N-hydroxy-succinimidyl)-ester according to the manufacturer's instruction. Briefly, magnetic beads is resuspended in 0.1M sodium phosphate buffer with 0.15M NaCl, pH 7.4.

NHS-ester, DTSSP (3,3'-Dithiobissulfosiccinimidylpropionate) (Pierce, Rockford, Ill., USA; Cat #21578), is dissolved in water and added directly to the beads. Final volume is equal to the bead-volume originally pipetted from the vial. Reaction is mixed, and incubated 30 min at room temperature with slow tilt rotation. After incubation, the tube is placed on the Magnetic Particle Concentrator (Dynal MPC™-S, Invitrogen Corporation, Carlsbad, Calif. Cat #120.20D) for 4 min and supernatant is removed. Magnetic beads washed 2 more times with the buffer above. Finally NHS-ester activated magnetic beads is sequentially washed with ice-cold 1 mM HCl and ice-cold water. Then 0.7 ml Capture Antibody 1 is added and incubated for 2 hrs at 4° C. with slow tilt rotation. (Usually 10-fold molar excess of NHS-ester crosslinker is used compared to the amount of antibody to be immobilized. For antibody coating of Dynabeads® M-270 Amine, 3 ug pure antibody per 107 beads and final concentration of 1–2×10$^9$ beads per ml is recommended).

After incubation, tube is placed on the Magnetic Particle Concentrator for 4 min and supernatant is removed. 0.05M Tris pH7 is added and incubated for 15 min at room temperature with slow tilt rotation, to quench non-reacted groups.

Magnetic beads washed 4 times in buffer containing PBS and 0.5% BSA. After the final wash the coated beads is resuspended in PBS and 0.1% BSA to 1 10$^9$ beads/ml. For storage of the Capture Antibody 1 coated magnetic beads 0.02% sodium azide is added and kept at 4° C.

Example XVI

Binding of Target Agent and Removal of Excess Antibody-Enzyme Conjugate (Model System Study)

Capture Antibody 2, an anti-Mouse α-Human IL-8 Monoclonal Antibody (for ICC, BD Pharmingen cat #550419) is conjugated to a Glucose Oxidase from *Aspergillus niger* (Fluka, 49180) according to the procedure for conjugation described in Example XVI. Capture Antibody 1, an anti-Mouseα-Human IL-8 Monoclonal Antibody (ELISA capture, BD Pharmingen cat #554716) immobilized aminoderivatized magnetic beads (Dynabeads® M-270 Amine, Invitrogen Corporation, Carlsbad, Calif. Cat #610) is prepared according to the procedure for immobilization described above.

Above mentioned monoclonal antibodies represent a pair recognizing two different epitopes of recombinant Human IL-8.

To reconstitute a model system 0.5 ug of Protein Target Agent, recombinant Human IL-8 (BD Pharmingen cat #554609, 0.1 mg/ml) is spiked into FBS (Fetal Bovine Serum) along with Capture Antibody 2—Glucose Oxidase conjugate (typically 20 ug is used).

15 ug (30 ul) of Capture Antibody 1 immobilized magnetic beads is blocked by mixing with Fetal Bovine Serum for 45 min at room temperature. The resulting reaction mixture is placed on the Magnetic Particle Concentrator and supernatant is discarded.

Above mentioned reconstituted model system (Human IL-8 and Capture Antibody 2—Glucose Oxidase conjugate) is added to the washed Capture Antibody 1—magnetic beads and the volume of reaction mixture is brought to 500 ul with PBS.

The reaction mixture, after adding to it BSA to a final concentration of 1 mg/ml, is incubated at room temperature with slow tilt rotation.

Unbound Capture Antibody 2—Glucose Oxidase conjugate is removed by washing with PBS (7 times). After the last wash the supernatant is carefully removed, remaining magnetic beads are resuspended in 10 ul of 2M Potassium Phosphate Buffer (pH 6.0) and kept at 4° C.

The Target Agent bound Capture Antibody 2—Glucose oxidase conjugate remains on the magnetic beads and is available for detection.

In parallel, as a negative control, similar reaction is set up with no Target Agent (Human IL-8) spiked into FBS (Fetal Bovine Serum).

Example XIX

Detection of Protein Target Agent Bound Magnetic Beads (Model System Study)

A Protein Target Agent bound magnetic beads is prepared according to the capture procedure described previously. Resulted 10 ul of Target Agent bound magnetic beads is washed (2 times) with 100 ul of 2M Potassium Phosphate Buffer (pH 6.0).

Each time magnetic beads are separated using Magnetic Particle Concentrator (Dynal MPC™-S, Invitrogen Corporation, Carlsbad, Calif. Cat #120.20D). After the last was the supernatant is carefully removed, remaining magnetic beads are resuspended in 2-5 ul of buffer containing 2M Potassium Phosphate Buffer (pH 6.0), 0.1 mM DCPIP (2,6-Dichloroindophelol, 0.1 ug/ul BSA).

In parallel a Detection Cell is assembled. Detection Cell contains 2 reaction chambers (anode and cathode reaction chambers) separated by NAFION Membrane N-117 (FuelCellStore, San Diego, USA).

Each reaction chamber has gold electrode inserted in it. Gold electrodes are connected to Fluke 289 True-RMS Industrial Logging Multimeter with TrendCapture (Fluke, Everett, Wash., USA) to take potentiometric or amperometric measurements.

20 ul of Working Buffer (2M Potassium Phosphate Buffer (pH 6.0), 0.1 mM DCPIP (2,6-Dichloroindophelol)) is added to each reaction chamber. 1 ul of Target bound magnetic beads is mixed with 1 ul of 1M glucose and transferred into anode reaction chamber. Potentiometric measurements are taken continuously or every 5 minutes of interval. Presence of the Protein Target Agent is detected by measurements of increasing potential (1-55 mV range).

During the measurements of the negative control reaction no potential is detected.

Specific Operating Embodiment

Further information regarding the performance of this invention may be had by discussion of basic reagents and procedures of this invention. Like each of the examples discussed above, it relies on the generation of electric potential, which can be detected by the working cell of the portable test unit of the invention. That test unit can accept a test module (disposable) which comprises an membrane, or a membrane free measurement chamber. In a preferred embodiment, the test chamber is a plastic well which is supported on a vertical flange on which are painted the two electrodes, separated by an operative distance across which a potential can be measured by closing a circuit. The electrodes can be painted on the test chamber backing, and may be preferably be made of gold. In a preferred embodiment, the cathode is overlaid with a film of Nafion of similar polymeric material.

Reagents & Testing Procedures

A. Reagents. The following reagents are the standard reagents used in the SASP testing. All reagents are commercially available. The time needed for sample prep (using standard molecular biology techniques) accounts for 95% of the time needed to complete the detection assay. Optimization of the sample prep through automation and robotics can significantly reduce the duration of the assay. Oligonucleotides and other listed nucleic acid sequences intended for use as model/control reagents.

1. First Complexing ("FC") oligonucleotide [SEQ ID NO.: 2] #100003_19_polyA (36 nucleotides):

5'-GTGATCGGGAGTGTGTCCAAAAAAAAAAAAAAAAAA-3'

Second Complexing ("SC") oligonucleotide [SEQ ID NO.: 1] #100003_15_amino (5'-NH$_2$modified 15 nucleotides):

5'-AGGATGACACCTAGA-3'

Target Specific ("TS") oligonucleotide [SEQ ID NO.: 3] 100003_39 (39 nucleotides)

5'-TGGACACACTCCCGATCACCACGATCTAGGTGTCATCCT-3'

Dynabeads Oligo (dT)$_{25}$ magnetic beads
Dynabeads® M-270 Amine
Dynal MPC™-S Magnetic Particle Concentrator
Glucose Oxidase from *Aspergillus niger*
D-glucose
DCPIP (2,6-Dichlorophenolindophenol)
Lightning-Link Glucose Oxidase Congugation Kit
Human Genomic DNA
ssM13mp18
NAFION Membrane N-117
Liquid Nafion, LIQGUION™ Solution All other chemicals and materials, necessary to make standard buffers and solutions, were purchased from Sigma-Aldrich, Pierce Biotechnologies and/or VWR.

Standard Buffers:
1. 1× Binding Buffer (20 mM Tris-HCl, pH 7.5, 1.0M LiCl, 2 mM EDTA).
2. Washing buffer B (10 mM Tris-HCl, pH 7.5, 0.15M LiCl, 1 mM EDTA).
3. Storage Buffer (250 mM Tris-HCl, pH 7.5, 20 mM EDTA, 0.1% Tween-20, 0.02% NaN$_3$).

B. Testing Procedure. The following description is provided for a "two-step" hybridization. It has however, been empirically determined that a one-step hybridization (i.e., performing the hybridization steps in a single reaction vessel) can beneficial.

1. Experimental Setup
   a. FC oligonucleotide is purified using NAP-5 column (0.1M/0.15M buffer of NaHCO$_3$/NaCl, pH 8.3). following the manufacturers protocol. Briefly, 0.2 ml of 100 uM water solution of oligonucleotide #100003_15_amino is loaded on a column. After 0.3 ml push 0.8 ml of eluant is collected and quantified. Based on A$_{260}$ reading more than 90% of recovery should be observed.
   b. Purified FC oligonucleotide is annealed with Oligo (dT)$_{25}$ magnetic beads.
   c. 30 ul of the foregoing magnetic beads suspension is washed twice with 1× Binding Buffer (20 mM Tris-HCl, pH 7.5, 1.0M LiCl, 2 mM EDTA). Magnetic beads are separated using a magnetic particle concentrator following each wash.
   d. Following final wash the beads are resuspended in 30 ul of Binding Buffer and mixed with 2.6 ul of FC oligonucleotide (26 pmole). The final reaction volume is adjusted to 45 ul final volume by the addition of DDI water/0.01% Tween 20, and incubated at room temperature with continuous rotation (~30-45 min).
   e. Following incubation the annealed magnetic beads are separated using a magnetic particle concentrator and the supernatant is discarded. The Magnetic beads are washed (3 times) with Washing buffer B (10 mM Tris-HCl, pH 7.5, 0.15M LiCl, 1 mM EDTA), washed once with Storage Buffer Oligo (dT)$_{25}$ (250 mM Tris-HCl, pH 7.5, 20 mM EDTA, 0.1% Tween-20, 0.02% NaN$_3$), and resuspended in 30 ul of Storage Buffer Oligo (dT)$_{25}$. The final solution can be stored at 4° C. for future use.

2. Test Cell Conditioning
   The test cell is pre-conditioned to remove positive background by washing the cell with dH20 (10× 50 ul) followed by "shorting" the cell (accomplished via scripting) for 120 seconds.

3. Sample Assaying
   a. The SC oligonucleotide is purified using the same basic protocol as set forth above for the FC oligonucleotide. Purified SC oligonucleotide is conjugated with Glucose Oxidase using the commercially available Lightning-Link Glucose Oxidase Congugation Kit pursuant to the manufacturer's recommended protocol with minor modifications. Briefly, 4 ul of the modifier is added to 40 ul of amino-modified SC oligonucleotide (50 uM in water). The resulting solution is admixed with ½ vial of LL-Gox and incubated overnight in the absence of ambient light and at room temperature. Following overnight incubation, 5 ul of quencher is added to the reaction mixture and incubated for 30 min in the absence of ambient light at room temperature.
   b. The resulting conjugate is purified by centrifugation through a Micron YM-100 spin column (Millipore, USA) to remove unreacted amino modified oligonucleotide. For best results, 50 ul of the resulting conjugate is loaded onto the column and centrifuged at 8000 rpm for 8 min. Flow through is discarded and 200 ul of 1× (50 mM) PBS (50 mM, pH 7.5) is added to the column and centrifuged at 8000 rpm for 8 min. The flow through is once again discarded and 50 ul of 1×PBS (50 mM, pH 7.5) is added to a column, carefully mixed using a vortex for 5-10 seconds, followed by centrifugation at 2000 rpm for 2 min. The resulting 50 ul of purified SC oligo-Enzyme conjugate is collected and can be stored at 4° C. for future use.
   c. TS oligonucleotide is purified in a manner similar to that described above for the FC and SC oligonucleotides.
   d. TS oligonucleotide (0.5-100 fmol) is added to 1 ug of Human Genomic DNA (or ssM13mp18 plasmid DNA) with 0.5 pmol of Conjugate. The total reaction volume should be approximately 30 ul (6×SSPE, 0.01% Tween 20). The resulting reaction mixture is transferred into a tube containing 0.5 pmol of washed, dry FC immobilized-Oligo (dT)$_{25}$ magnetic beads and gently mixed. Hybridization is conducted at room temperature with continuous rotation for 1 hr.
   e. With the magnetic field in place, unbound Conjugate is removed by washing (3 times) with 6×SSPE (0.9M NaCl, 60 mM NaH$_2$PO$_4$, 6 mM EDTA). Following washing, the supernatant is carefully removed by pipetting and the Target-magnetic bead complex ("Complex") washed (2 times) with 100 ul of 2M Potassium Phosphate Buffer (pH 6.0) and resuspended in 2-5 ul of buffer containing 2M Potassium Phosphate Buffer (pH 6.0), 0.1 mM DCPIP (2,6-Dichloroindophelol, 0.1 ug/ul BSA).

f. In parallel with the foregoing steps, a negative control is prepared wherein the reaction is performed without the inclusion of the TS oligo and Human Genomic DNA (or ssM13mp18 plasmid DNA).

g. Using the Detection Cell (type 1), 30 ul of Working Buffer (2M Potassium Phosphate Buffer (pH 6.0), 0.1 mM DCPIP (2,6-dichloroindophenol) is added to each (anode and cathode) reaction chamber. To assay for the presence (or absence) of the target species, 1 ul of the Complex and 1 ul of 1M glucose are added to the anode reaction chamber and thoroughly mixed.

h. The reaction is allowed to incubate for 5 min, after which measurements are taken continuously or every 30-180 seconds of interval. The presence of the target species is represented by signals of increasing potential (0.4-2.2V range). (see, representative output FIG. 2, below).

Apparatus Optimized for Portable Use

As noted, the assays made possible by this invention are susceptible of practice in a wide variety of apparatus. Particularly desirable apparatus will be portable, for deployment in the field. One such apparatus is described, by way of exemplification rather than limitation, below. Alternatives will occur to those of skill in the art without the exercise of inventive faculty.

The Chemical Demonstration Unit Workstation Software controls timing and recording of measurements. This document only describes the workstation software and not the complete system. The PC workstation is connected via USB to a Data Acquisition board (Data Acquisition DT9812). The board controls reading to the Amplifier circuitry using the digital outputs, and analog inputs. The circuitry is connected to the Chemistry Cell Cartridge where the GOX Cell is housed.

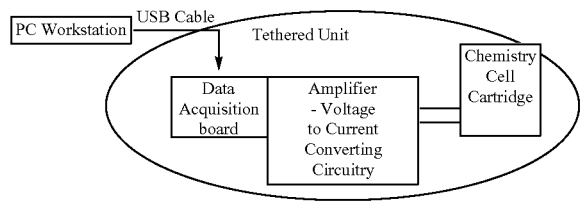

The needs of the invention are met by a portable system that relies on a combination of hardware and software to deliver a clear, reliable signal. The current version is being developed with dotNet 2.0 using Microsoft Visual Studio 2005.

The workstation currently uses the Data Translation DT9812 data acquisition board connected via standard USB 2.0. Data Translation provides Windows XP drivers as well as a dotNet API library. The circuit board makes use of the DT9812 digital outputs for controlling the switches on the circuit, and uses the DT9812's analog input for voltage measurements.

Installation Procedure—The installation and use of the workstation requires specific functionalities. First the workstation preferably needs to be running Windows XP with Service Pack 2. Windows dotNET Version 2.0 preferably needs to be installed. Data Translation provides a CD containing the Windows Drivers and the dotNET API, both need be installed first. Then DT9812 needs to be plugged in next for the system to recognize the device and use the installed drivers. For internal development use, the latest version of the workstation will be checked for on the intranet website which may be accessed via codeguest: 8080/apps/Box3 Other installations will have different installation procedures.

Reference is made to U.S. Provisional Patent Application Ser. No. 60/834,951, filed Aug. 2, 2006, currently pending; U.S. Provisional Patent Application Ser. No. 60/851,697, filed Oct. 13, 2006, currently pending; U.S. Provisional Patent Application Ser. No. 60/853,697, filed Oct. 23, 2006, currently pending; U.S. Provisional Patent Application Ser. No. 60/859,441, filed Nov. 16, 2006, currently pending; U.S. Provisional Patent Application Ser. No. 60/874,291, filed Dec. 12, 2006, currently pending; U.S. Provisional Patent Application Ser. No. 60/876,279, filed Dec. 21, 2006, currently pending; and U.S. patent application Ser. No. 11/703,103, filed Feb. 7, 2007, currently pending, each of which are herein incorporated by reference in their entireties for all purposes.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

---

What is claimed is:

1. An assay system for the detection of a target in a liquid sample, wherein said assay system consists essentially of:
    a first capture moiety which binds to any target present in said sample, said first capture moiety complexed with an enzymatic redox reaction component, wherein the enzymatic redox reaction component is an oxidase or dehydrogenase of a substrate;
    a second capture moiety which binds to any said target present in said sample in a way not to interfere with binding of said first capture moiety to said target, said second capture moiety being bound to an element that facilitates separation of target bound thereby from the remainder of said sample;
    the substrate recognized by said enzymatic redox reaction component, wherein the substrate, when acted upon by said enzymatic redox reaction component, releases electrons; and
    an electronic circuit configured for self-actuating signal producing detection of the presence of electric potential, electric current, or both, developed by the release of electrons from said substrate when digested by said enzymatic redox reaction component, wherein said electric potential or said electrical current is detected in the absence of any source of electrical power provided to said assay system other than electrical power generated by the release of electrons from said substrate when digested by said enzymatic redox reaction component.

2. The assay system of claim 1, wherein said target is a protein, and said first and second capture moieties comprise different antibodies which bind to said target simultaneously.

3. The assay system of claim 1, wherein said element that facilitates separation comprises a collection of magnetic beads which is bound by a matrix over which said sample is run after addition of said second capture moiety.

4. The assay system of claim 1, wherein said substrate glucose and said enzymatic redox reaction component is glucose oxidase.

5. The assay system of claim 1, further consisting essentially of a reaction chamber wherein said first capture moiety coupled with said enzymatic redox reaction component, said second capture moiety bound to a collection moiety, said sample and said substrate are combined, said assay system further comprising an anode and a cathode connected to said reaction chamber, wherein a potential or current developed across said cathode and anode due to generation of electrons by action on said substrate by said enzymatic redox reaction component is detected as evidence of the presence of target in said sample.

6. An assay method for detecting the presence of a target in a sample, said method comprising using the assay system of claim 1 wherein said first capture moiety and said second capture moiety are combined with said sample under conditions which permit binding of said first and second capture moiety to any said target in said sample, any said target in said sample bound by said first and second capture moieties is retained by retaining a collection moiety, thereafter said substrate is added to said bound target, wherein any potential or current generated by reaction between said oxidase or dehydrogenase and said substrate is detected as a signal reflecting the presence of said target in said sample.

7. The method of claim 6, wherein said target comprises an amino acid sequence, and said first and second capture moieties comprise different antibodies which bind to said target simultaneously.

8. The method of claim 6, wherein said substrate is glucose and said enzymatic redox reaction component is glucose oxidase.

9. The method of claim 6, wherein said first capture moiety and second capture moiety are added to said sample sequentially.

10. The method of claim 6, wherein said first capture moiety and second capture moiety are added to said sample simultaneously.

11. The method of claim 6, wherein said signal is communicated to a computer which stores said signal.

12. The method of claim 11, wherein said computer communicates the signal to a signal receiving device different than said computer.

13. The method of claim 6, wherein the strength of said signal is correlated with the amount of said target present in said sample.

14. The method of claim 6, wherein said signal is not detected for a period of time of at least one minute following addition of said substrate to said separated target.

* * * * *

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: second complexing ("SC") oligonucleotide
      #100003_15_amino (5'-NH2 modified 15 nucleotides)

<400> SEQUENCE: 1
aggatgacac ctaga                                                        15

<210> SEQ ID NO 2
<211> LENGTH: 36
```

```
<212> TYPE: DNA
<213> ORGANISM: Artificial Sequence
<220> FEATURE:
<223> OTHER INFORMATION: first complexing ("FC") oligonucleotide
      #100003_19_polyA (36 nucleotides)

<400> SEQUENCE: 2
gtgatcggga gtgtgtccaa aaaaaaaaaa aaaaaa                                36

<210> SEQ ID NO 3
<211> LENGTH: 39
<212> TYPE: DNA
<213> ORGANISM: Artificial Sequence
<220> FEATURE:
<223> OTHER INFORMATION: target specific ("TS") olignucleotide 100003_39
      (39 nucleotides)

<400> SEQUENCE: 3
tggacacact cccgatcacc acgatctagg tgtcatcct                             39
```